United States Patent [19]

Magni et al.

[11] Patent Number: 4,834,919

[45] Date of Patent: May 30, 1989

[54] STEREOSELECTIVE REDUCTION OF THE KETO GROUP AT 7-POSITION OF A BILE KETO ACID

[75] Inventors: Ambrogio Magni, Osnago; Oreste Piccolo, Leghorn; Antonio Ascheri, Vedano al Lambro, all of Italy

[73] Assignee: Blaschim S.p.A., Milan, Italy

[21] Appl. No.: 868

[22] Filed: Jan. 6, 1987

[30] Foreign Application Priority Data

Jan. 9, 1986 [IT] Italy ................................ 19038 A/86

[51] Int. Cl.$^4$ ................................................. C07J 1/00
[52] U.S. Cl. .................................................. 260/397.1
[58] Field of Search ...................................... 260/397.1

[56] References Cited
PUBLICATIONS

Chemical Abstracts; vol. 96 (1982) #20375m; Faba et al.
Chemical Abstracts; vol. 97 (1982) #127928s; Tokyo Tanabe Co. Ltd.
Chemical Abstracts; vol. 97 (1982) #163327d; Laboratofres Arkodex.
Chemical Abstracts; vol. 87 (1977) #201897t; Suzuki et al.

*Primary Examiner*—Douglas W. Robinson
*Assistant Examiner*—Joseph A. Lipovsky
*Attorney, Agent, or Firm*—Cushman, Darby & Cushman

[57] ABSTRACT

The keto group at the 7-position of a bile keto acid is stereoselectively reduced to a beta-hydroxy group with hydrogen in the presence of nickel, a base (the quantity of which is at least 0.3 mole for each mole of keto acid), and an alcohol having from 3 to 10 C atoms, selected from the group consisting of secondary alcohols, tertiary alcohols and beta-branched alcohols.

8 Claims, No Drawings

STEREOSELECTIVE REDUCTION OF THE KETO GROUP AT 7-POSITION OF A BILE KETO ACID

The present invention relates to a process for stereoselectively reducing the keto group at the 7-position of a bile keto acid to a beta-hydroxy group using hydrogen in the presence of nickel, a base (the quantity of which is at least 0.3 mole for each mole of keto acid), and an alcohol having from 3 to 10 C atoms, selected from the group consisting of secondary alcohols, tertiary alcohols and beta-branched alcohols.

The term "beta-branched alcohols" as used herein indicates a compound of the formula:

$$R-\underset{\underset{R_2}{|}}{\overset{\overset{R_1}{|}}{C}}-CH_2OH \qquad (III)$$

wherein R, $R_1$ and $R_2$, which may be the same or different, are hydrogen, alkyl or phenyl, provided that at least two of the radicals, R, $R_1$ and $R_2$, are different from hydrogen.

Preferably, the process of this invention relates to the reduction of a bile keto acid of the formula;

(I)

wherein

R is H, an alkyl having from 1 to 10 C atoms, $Si(R'')_3$ or a cation, wherein in turn R'', which may be the same or different, is an alkyl having from 1 to 6 C atoms or phenyl;

X' is OH, OR', OCOH, OCOR' or $OSi(R'')_3$, wherein in turn R' is an alkyl having from 1 to 10 C atoms optionally substituted by phenyl or fluorine, or an optionally substituted aryl, and R has the abovementioned meanings;

X is H or, together with X', is an oxygen atom;

Y' is H, OH, OR', OCOH, OCOR', $OSi(R'')_3$ or $OSO_2R'$, wherein R' and R'' have the above-mentioned meanings;

Y is H or, together with Y', is an oxygen atom or, together with Z, is a covalent bond; and Z is H or, together with Y, has the above-mentioned meaning;

to prepare a compound of the formula:

(II)

wherein R, X, X', Y, Y' and Z have the above-mentioned meanings.

Specific examples of cations (with regard to formula (I)) are sodium, potassium, calcium and magnesium.

R' is preferably methyl, ethyl, propyl, butyl, hexyl, trifluoromethyl, phenyl, p-methylphenyl, benzyl or naphthyl.

R'' is preferably methyl, ethyl, isopropyl, tert-butyl or phenyl.

It is known that the carbonyl group at the 7-position of a bile keto acid can be converted into a hydroxy group by means of various reducing systems.

In accordance with the reducing system which is used, the resulting hydroxy group has an alpha or a beta configuration; an epimeric mixture is thus obtained, when the reducing system is not stereoselective.

It is also known that the preparation of the alpha epimer in a substantially pure form is not particularly difficult.

Suitable reducing agents which may be used to prepare the alpha epimer are, for example, sodium dithionite and sodium borohydride in basic medium (Tetrahedron Letters, 2487, 1983) and K-Selectride (Tetrahedron, 40, 851, 1984).

In contrast, a reducing system which provides the beta epimer in a substantially pure form is not yet known. There are only known some systems which provide epimeric mixtures wherein the amount of the beta epimer predominates.

Said reducing systems consist of a metal, such as sodium, potassium or zinc, and an alcohol or liquid ammonia; the ratio of the beta epimer to the alpha epimer ranges in accordance with the experimental conditions, the kind of solvent used, the nature of the metal and the like (Angew. Chem. Int. Ed. Engl. 24, 499 (1985); Tetrahedron Letters 2487 (1983); Japanese Kokai Tokyo Koho 82-56497 (C.A. 97, 127928s, 1982); French Application 2,453,182 (C.A. 97, 163327d, 1982); Spanish Pat. No. 489,661 (C.A. 96, 20375m, 1982); Japanese Kokai No. 77-07950 (C.A. 87, 1668274n); Acta Chem. Scand. 14, 17 (1960)).

The greatest stereoselectivity towards the beta epimer (about 95/5) is obtained when there is used an alkali metal, in particular potassium, and a tertiary alcohol.

However, this process requires special safety measures and can be performed only on a relatively small scale because of the known inflammability of the alkali metals which are used in great excess.

Therefore, there is still a need for a highly stereoselective, cheap and safe process for reducing the keto group at the 7-position of a bile keto acid to a beta-hydroxy group.

Now, it has surprisingly been found that this object can be achieved using hydrogen in the presence of nickel, a base (the quantity of which is at least 0.3 mole for each mole of keto acid), and an alcohol having from 3 to 10 C atoms, selected from the group consisting of secondary alcohols, tertiary alcohols and beta-branched alcohols of the formula:

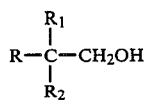

$$R-\underset{R_2}{\overset{R_1}{C}}-CH_2OH \quad (III)$$

wherein R, $R_1$ and $R_2$, which may be the same or different, are hydrogen, alkyl or phenyl, provided that at least two of the radicals, R, $R_1$ and $R_2$, are different from hydrogen.

A further advantage of the process of this invention is that it does not require an especially pure nickel; therefore a commercial nickel which incorporates other metals, such as Raney nickel, can be used.

The results obtained using the process of this invention are even more unexpected when considering that:

(a) In the presence of Raney nickel, hydrogen stereoselectively reduces the keto group at the 3-position and not the keto group at the 7-position. In fact, Japanese Patent Application No. 77-78864 (C.A. 87, 201897t (1977)) discloses a process for preparing ursodeoxycholic acid (UDCA) wherein, in a first step, the keto group at the 3-position of a compound of formula (I) (wherein R=Z=Y=Y'=H; and X+X'=O) is reduced with hydrogen and Raney nickel to give the corresponding compound wherein X is hydrogen and X'=alpha-OH, without affecting the keto group at the 7-position. This keto group is then reduced with potassium and tert-butanol to give a mixture consisting mostly of the beta epimer.

(b) As already seen before, when Raney nickel is absent, the hydrides generate the alpha epimer.

(c) Raney nickel favors the epimerization of the steroid hydroxy groups, such as, for example, those at the 3-position, possibly through formation of keto intermediates, and/or favors isomerization of the steriod rings A/B cis to A/B trans (J. Org. Chem. 33, 175 (1968); ibid. 33, 2814 (1968); ibid. 44, 4567 (1979); Tetrahedron Letters 2085 (1979)).

An essential feature of the process of this invention is the presence of a base, the quantity of which is at least 0.3 mole for each mole of keto acid.

The absence of the base spoils the reducing capacity of the system when hydrogen is used (Example 3) or causes the alpha epimer to predominate when a hydride is used (Example 2).

Quantities lower than 0.3 mole give unsatisfactory results with regard to the yields and the repeatability of the process.

The quantity of base is preferably in the range of from 0.3 to 2 moles to each equivalent of keto group.

Examples of suitable bases are the alkali and alkaline earth metal alcoholates, phenates, carbonates, hydroxides and the like.

Examples of preferred bases are sodium and potassium tert-butylate, isopropylate, tert-amylate, methylate and phenate, potassium carbonate and hydroxide.

The amount of nickel with respect to the bile keto acid is preferably in the range of from 0.1 to 2 (w/w).

The alcohols may be either alicyclic or cyclic. Examples of suitable alcohols are isopropyl, tert-butyl, sec-butyl, tert-amyl, isobutyl and neopentyl alcohol, 2-pentanol, 1-phenyl-ethanol and cyclohexanol.

Hydrogen may also be generated "in situ" by suitable hydrogen donors.

Examples of hydrogen donors are secondary alcohols and hydrides, such as sodium and potassium borohydride, and tributyl tin hydride.

Preferred conditions are as follows:
Temperature: 0°–150° C., and preferably, 20°–85° C.;
Pressure: 1–10 atm, and preferably, 1 to 4 atm;
Reaction time: 2–50 hrs.

According to this invention, at lease 90% of the keto group at the 7-position is reduced and the obtained product contains up to 98% of beta epimer.

When the bile keto acid contains other keto groups, such as, for example, at the 3 and/or the 12-position, they also may be reduced using the process of this invention. In such a case, the amount of the reactants will be adjusted in accordance with the expected result and the base may amount to 3 moles for each mole of keto acid.

When carrying out the process of this invention, the ester groups which may be present in compound (I) may undergo hydrolization and the $OSO_2R'$ group may undergo elimination with the formation of a double bond.

The advantages offered by this invention will become evident to the artisan through the present disclosure and the following examples which are intended to illustrate this invention without limiting it.

EXAMPLE 1

Potassium 3-alpha-hydroxy-7-oxo-5-beta-cholanate (9.05 g; 21.1 mmol), isopropyl alcohol (450 ml) and potassium tert-butylate (2.74 g; 24.4 mmol) were added to Raney nickel (9.5 g) in nitrogen atmosphere. Hydrogen was added and the reaction mixture was maintained at 40° C. at atmospheric pressure while the course of the reaction was monitered using HPLC analysis.

When the reaction was complete, stirring and heating were stopped. The alcoholic phase was separated and the solvent was removed by evaporation.

The residue was treated with water (200 ml) and the thus obtained solution was made acidic using 1 N hydrochloric acid. The precipitate was collected by filtration, washed with water and dried.

A mixture (7.90 g; yield, 95%) of ursodeoxycholic acid (UDCA; 7.63 g; 97%) and of chenodeoxycholic acid (CDCA; 0.27 g; 3%) was thus obtained.

Analogous results were obtained using the same method as described above with the exception that the following replacements were made:

isopropyl alcohol was replaced with tert-butyl alcohol and the reaction mixture was heated at 80° C. instead of at 40° C.;

isopropyl alcohol was replaced with pentan-2-ol and the reaction mixture was heated at 60° C. instead of at 40° C.;

isopropyl alcohol was replaced with sec-butyl alcohol or isobutyl alcohol;

isopropyl alcohol was replaced with neopentyl alcohol and the reaction mixture was heated at 50° C. instead of at 40° C.;

potassium tert-butylate was replaced with sodium hydroxide, potassium carbonate or phenate;

Raney nickel was replaced with commercially pure nickel without adding hydrogen and using isopropyl alcohol as the hydrogen donor at 81° C.;

hydrogen was replaced with potassium borohydride (3 g; 55.6 mmol).

EXAMPLE 2

Potassium 3-alpha-7-oxo-5-beta-cholanate (2 g; 4.67 mmol) was added to a suspension of Raney nickel (2 g) in isopropyl alcohol (80 ml). Potassium borohydride (0.63 g; 11.68 mmol) was then added.

The mixture was stirred at 40° C. until reduction was complete (HPLC analysis).

Finally, the reaction mixture was treated as indicated in Example 1 above.

A mixture containing 65% of CDCA, 10% of UDCA and 25% of the starting product was thus obtained.

EXAMPLE 3

No reduction product was obtained using the same method described in Example 1 with the exception that potassium tert-butylate was not used.

EXAMPLE 4

Potassium 3,7-dioxo-5-beta-cholanate (2 g; 4.7 mmol), isopropyl alcohol (80 ml) and potassium tert-butylate (1.15 g; 10.3 mmol) were added to Raney nickel (2 g) in nitrogen atmosphere. Hydrogen was added and the reaction mixture was maintained at 40° C. and at atmospheric pressure, while monitoring the course of the reaction using HPLC analysis.

When reduction was complete, stirring and heating were stopped. The alcoholic phase was separated and the solvent was removed by evaporation.

The residue was treated with water (40 ml) and the thus obtained solution was made acidic using 1 N hydrochloric acid. The precipitate was collected by filtration, washed with water and dried.

A mixture (1.75 g) of UDCA (98%) and CDCA (2%) was thus obtained. The conversion was 96%.

EXAMPLE 5

The method of Example 4 was repeated with the exception that potassium 3,7-dioxo-5-beta-cholanate was replaced with the trimethylsilyl ester of 3-alpha-trimethylsilyloxi-7-oxo-5-beta-cholanic acid (1.8 g; 3.3 mmol), and 0.92 g (8.2 mmol) of potassium tert-butylate was used.

A mixture (1.21 g) was thus obtained containing 3% of 3-alpha-hydroxy-7-oxo-5-beta-cholanic acid and 97% of UDCA/CDCA (96/4).

EXAMPLE 6

Potassium 3-alpha-hydroxy-7-oxo-5-beta-cholanate (3.6 g; 8.4 mmol), isopropyl alcohol (120 ml) and potassium isopropylate (0.25 g; 2.5 mmol) were added to commercially pure nickel (2.8 g) in nitrogen atmosphere.

The reaction mixture was refluxed for 2 hours, following which the method of Example 4 was followed.

The conversion was 60%; UDCA/CDCA=94/6.

The process was repeated with;

0.42 g (4.1 mmol) of potassium isopropylate; conversion, 80%; UDCA/CDCA=95/5;

0.84 (8.2 mmol) of potassium isopropylate was used and the reaction mixture was refluxed for 3 hrs; conversion, 93%; UDCA/CDCA=95/5.

We claim:

1. A process for reducing stereoselectively the keto group at 7-position of a bile keto acid to beta hydroxy group wherein the keto acid is reduced with hydrogen in the presence of:

(a) nickel, the quantity of which with respect to the bile keto acid is in the range of 0.1 to 2 (w/w), (b) a base, the quantity of which is at least 0.3 mole to each mole of keto acid, and (c) an alcohol, having from 3 to 10 C atoms, selected from the group consisting of secondary alcohols, tertiary alcohols and beta-branched alcohols of the formula

$$R-\underset{\underset{R_2}{|}}{\overset{\overset{R_1}{|}}{C}}-CH_2OH \qquad (III)$$

wherein R, $R_1$ and $R_2$, the same or different, are hydrogen, alkyl, or phenyl, provided that at least two of the radicals R, $R_1$ and $R_2$ are different from hydrogen and, the process is carried out at a temperature in the range of 0–150° C. and at a pressure of 1–10 atm.

2. A process according to claim 1 above wherein a bile keto acid of the formula:

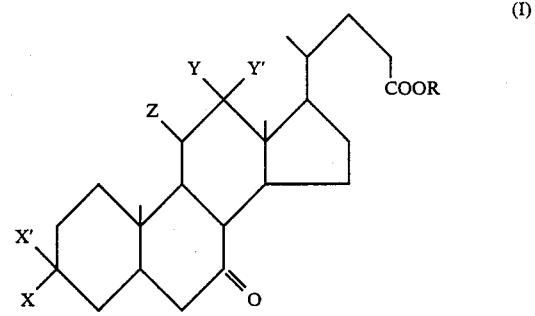

where

R is H, an alkyl having 1–10 C atoms, $Si(R'')_3$, or a cation, wherein in turn R'', the same or different, are alkyl having from 1 to 6 C atoms or phenyl;

X' is OH, OR', OCOH, OCOR', $OSi(R'')_3$ wherein in turn R' is an alkyl having 1–10 C atoms, optionally substituted by phenyl or fluorine, or an aryl optionally substituted, and R'' has the above mentioned meanings;

X is H or, together with X', is an oxygen atom;

Y' is H, OH, OR', OCOH, OCOR', $OSi(R'')_3$, $OSO_2R'$ wherein R' and R'' have the above mentioned meanings;

Y is H or, together with Y', is an oxygen atom or, together with Z, is a covalent bond;

Z is H or, together with Y, has the above mentioned meaning;

is reduced to prepare a compound of the formula:

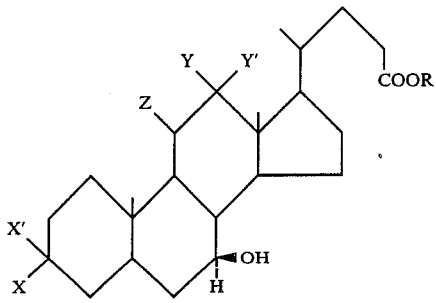

(II)

wherein R, X, X', Y, Y' and Z have the above mentioned meanings.

3. A process according to claim 1 above, wherein 3alpha-hydroxy-7-oxo-5beta-cholanic acid and 3,7-dioxo-5beta-cholanic acid are reduced to ursodeoxycholic acid.

4. A process according to claim 1 above, wherein hydrogen is generated "in situ" by a hydrogen donor selected from the group comprising sodium borohydride, potassium borohydride, tributyl tin hydride, and secondary alcohols.

5. A process according to claim 1 above, wherein nickel is a commercially pure nickel or Raney nickel.

6. A process according to claim 1 above, wherein the base is an alcoholate, a phenate, a carbonate or a hydroxide of an alkali or alkaline earth metal.

7. A process according to claim 1 above, wherein the reaction is carried out at a temperature comprised from 20° C. to 85° C.

8. Process according to claim 1 above, wherein the reaction is carried out at a pressure comprised from 1 to 4 atm.

* * * * *